United States Patent [19]
Nellhaus

[11] Patent Number: 5,845,264
[45] Date of Patent: Dec. 1, 1998

[54] BAR CODE IDENTIFICATION OF DRUGS

[76] Inventor: Gerhard Nellhaus, 670 Vernon St. #207, Oakland, Calif. 94610

[21] Appl. No.: 612,372

[22] Filed: Mar. 7, 1996

[51] Int. Cl.⁶ ..................................................... G06F 17/60
[52] U.S. Cl. .................................. 705/28; 705/2; 235/375
[58] Field of Search .............................. 705/2, 3, 22, 28, 705/29; 715/3; 235/375

[56] References Cited

U.S. PATENT DOCUMENTS

| | | | |
|---|---|---|---|
| 4,818,850 | 4/1989 | Gombrich et al. | 235/494 |
| 4,835,372 | 5/1989 | Gombrich et al. | 235/375 |
| 4,857,713 | 8/1989 | Brown | 705/373 |
| 4,967,928 | 11/1990 | Carter | 221/2 |
| 5,129,974 | 7/1992 | Aurenius | 156/64 |
| 5,237,157 | 8/1993 | Kaplan | 235/375 |
| 5,463,209 | 10/1995 | Figh et al. | 235/383 |
| 5,542,420 | 8/1996 | Goldman et al. | 600/301 |
| 5,597,995 | 1/1997 | Williams et al. | 235/375 |

OTHER PUBLICATIONS

Anne Bush, "Technology turns the local corner drugstore into national pharmacy", Automatic I.D. News, Feb. 1, 1995.

US HHS, FDA, "Imprinting of Solid Oral Dosage Form Drug Products for Human Use–Final Rule", 58 FR 47948, Sep. 13, 1993.

Pete Lippman, "Bar Codes: An Introduction", reprinted from Industrial Launderer, Apr. 1988.

The Bar Code Book: Reading, Printing, and Specification of Bar Code Symbols, Palmer, Roger C., copyright 1989, pp. 11–45, 81–85, 91–99 and 172–175.

Bar Codes FAQ, Whiting, Jerry, copyright 1995, pp. 1–5.

*Primary Examiner*—Gail O. Hayes
*Assistant Examiner*—Alexander Kalinowski
*Attorney, Agent, or Firm*—Bielen, Peterson & Lampe

[57] ABSTRACT

A system for the identification of medications in pill, capsule, tablet, and caplet for the system including the placement of machine scannable bar code symbols on the surface of the medication and the identification of the medication by use of the bar code. The resulting identification information can be analyzed by a computer program, permitting both a drug identification and verification method for use by a doctor, pharmacist, emergency room or other medical staff, paramedics, law enforcement personnel, patient and/or family members, or indeed anyone who may need to know a drug's identity, and a tracking system by inclusion of the identification data into an appropriate information database to monitor an individual's prescription drug consumption and to alert of potential harmful drug interactions.

5 Claims, 3 Drawing Sheets

BAR CODE IDENTIFICATION OF DRUGS

BACKGROUND OF THE INVENTION

This invention relates generally to a system for identification of prescription medications that has a primary feature the placement of identification markers on the outside of the medication. Specifically, this invention relates to a system for prescription medication identification using bar code symbols placed on the outside of the medication.

The proliferation of new prescription medications created by advances in pharmacology and the steady increase of generics unfortunately has unintentionally created health problems when: (1) patents misidentify and thereby misuse their prescribed drugs; (2) patients suffer adverse drug interactions when two or more prescribed drugs taken concurrently combine in a harmful manner; or (3) doctors misprescribe medications based on a lack of information regarding the patient's history. Health problems based on these scenarios are likely to grow over time because the introduction of every new medication increases the number of potential interactions with the prior existing set of medications.

Several related problems occurring most frequently in the elderly population are beginning to receive attention in research publications such as *The Journal of the American Medical Association* (JAMA), as well as the popular press. A recent JAMA study based on review of nursing home subjects concluded that roughly 23% of Americans ages 65 and over are using at least one of twenty medications that are notorious for triggering insomnia, fainting spells, or amnesia among the elderly. The study also stated broader educational and regulatory initiatives are needed, and a companion JAMA editorial referred to this study as illuminating "the tip of the iceberg".

This widespread problem prevails despite the well-known medical technique doctors often employ, called the "brown-bag" test. The brown-bag test consists of a patient, typically elderly, being instructed to empty the contents of their medicine chest into a bag and then to bring the bag into the physician's office or to a pharmacist for analysis.

Additionally, physicians are beginning to trace health problems in the elderly to the overprescription of medications in amount or duration. This phenomena has been explained as the result of the human body's changing reaction to medications as part of the aging process.

Currently, patients and doctors who cannot readily identify a prescribed medication can attempt to consult a guide such as *The Physician's Desk Reference* (PDR) that contains a pictorial index of commonly prescribed drugs. However, the elderly patients most at risk for these problems probably fail to possess the visual or mental acuity necessary to complete these tasks, and even the professionals who can consult the PDR may fail to locate their medication because it is a generic equivalent not shown. For the physician to consult the PDR each time the identity of a drug is in question, is an imposition that is time consuming and hence an added cost of service.

The patient's recourse is to visit a physician, physician's assistant or pharmacist who will conduct a brown-bag test. A physician, health provider, or law enforcement agent who cannot identify a medication using the PDR may be forced to conduct expensive laboratory tests on the unknown medication.

This inventor has devised a graphical system to assist in the identification of drugs. This system is described in U.S. Pat. No. 5,031,937, issued 16 Jul. 1991, entitled, "Pictorial Guidance/Reminder System for Medication." The system includes a pictorial graphic representation showing the drug and providing for the use of such graphic representations for a medication table for scheduled taking of medications. Because of the many similarly appearing generic and proprietary drugs, visual identification is frequently difficult.

Recent trends in health care also indicate that patients are being placed at risk because of the increased workload on pharmacists. Several national pharmacy associations have identified the problems caused by increased cost-cutting pressures on pharmacists. Examples cited include patients receiving the wrong medication dosage or even the wrong medication. Pharmacists are often cited for failing to comply with state laws requiring patient notification and counseling upon receipt of prescribed medications.

The identification problems described above are solved when medications are individually labeled with bar code symbols that uniquely identify the medication, or class of medications, when the medication is scanned through a common bar code reader. The bar code reader is connected to a computer containing the appropriate software to translate the output provided by the bar code reader into a data identifier that can be referenced to a database table that operates as an index of bar code-medication pairs. The computer could then display the medication name plus additional information desired.

This identification system could be utilized both by the patient at home and by the dispensing pharmacist, and would increase patient safety while decreasing health care costs.

As early as 1989, individuals in the bar code community generally suggested that bar codes could be used by health care providers in areas such as patient billing, pharmacy, and bedside medication verification. However, there was no suggestion that this should extend to actually placing a bar code on the drug item itself.

This system can operate using at least one of the many commercially available bar code symbologies that meet desired requirements based on: (1) the number of unique codes available; (2) medication size constraints; and (3) error detection and correction tolerances. Once implemented, this system will eliminate nearly all human error in confirming medication identification and will serve as a low-cost medication verification system.

Additionally, this system could be incorporated into an extended system that includes a database containing individual patient medication histories, and a database of known harmful drug interactions. Through this system, a patient would then receive a brown-bag test at a pharmacy or medical office that would reveal potentially dangerous medication interactions that no individual pharmacist or physician could have discovered, because of incomplete medical records.

SUMMARY OF THE INVENTION

The bar code drug identification system is accomplished by: (1) the application of a bar code identifier to the outside surface of the medication; and (2) the programming of a central processing unit (CPU) that is connected to a bar code reader and able to convert the electrical signals input by the bar code reader into the appropriate computer output identifier corresponding to the medication scanned by the bar code reader.

1. Application of the Bar Code Identifier

Several bar code symbologies have been commercially developed that permit numbers or alphanumeric characters to be encoded as a series of dark vertical lines set against a light colored background. One reference is, *The Bar Code Book: Reading, Printing, and Specification of Bar Code Symbols,* Palmer, R. (1989, Helmers Publishing, Inc.).

The various symbologies differ in the character sets that can be encoded, the amount of error detection and correction, and the physical space necessary to encode a given amount of data. Specifications for each symbology are well-known in the bar code industry, and at least one symbology known as Code 49 was developed specifically to encode information on small objects. A two-row Code 49 symbol can encode 15 numeric characters.

The actual choice of symbology will depend on the resolution of the bar code symbol that can be printed on the outside of the medication. Drug manufactures currently use high resolution printing techniques to label medications in tablet form (for example, Rifater®), capsule form (for example, Prozac®), caplet form (for example, Tylenol®), and gelcap form (for example, Tylenol®). The labeling currently on these products is of sufficiently high resolution to permit the application of bar code symbols on the medications.

It is expected that the outer surface of some medications is too dark to allow the bar code reader to properly scan the symbol. In these instances it may be necessary to deposit a "white" or "light colored" patch on the area that is to receive the bar code symbol prior to imprinting the bar code symbol on the medication.

2. Programming of the CPU to Process the Bar Code Reader Input

A bar code system typically consists of a mechanical bar code reading device connected through data communications means to a data processing resource. It is currently possible to attach a bar code reading device to the RS-232C interface of a personal computer. It is also currently possible to attach a "wedge reader" to the keyboard interface of a personal computer which allows the bar code reading device to emulate typed data from the keyboard.

Currently available software packages can provide the software interface between the bar code reading device and the personal computer. This software can be configured to receive the input signals from the bar code reader, translate the signal into a bar code identifier symbol, and place the resulting symbol data into the memory of the personal computer.

This drug identification system includes computer software that retrieves the resulting symbol data and performs a data lookup operation to a database of symbol data identifiers that match the symbol data to information corresponding to the medication. This database could either reside on the personal computer or reside off-site and be connected to the personal computer via a network connection.

As an added feature, the database preferably includes a graphic image of the identified drug to provide further visual confirmation of the identity. Such a visual identification system was taught in my issued patent, U.S. Pat. No. 5,031,937, entitled "Pictorial Guidance/Reminder System for Medication", issued Jul. 16, 1991. In that system a doctor or patient configured a pictorial diagram that displayed picture graphics of medications, dosage information, and medication administration timing information.

These and other features will become apparent from a consideration of the Detailed Description of the Preferred Embodiments.

DETAILED DESCRIPTION OF THE PREFERRED EMBODIMENTS

Figure 1:
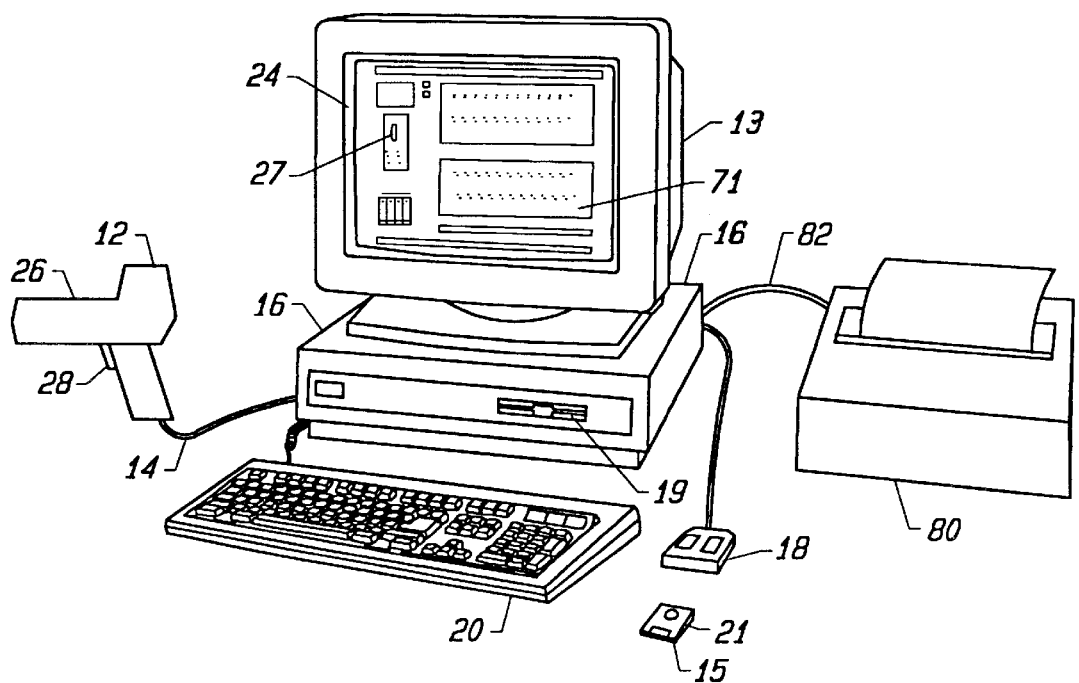
FIG. 1 is a perspective view of bar code identification of drugs system.

Referring to FIG. 1, the bar code identification of drugs system, designated generally by the reference numeral 10, is shown. In the preferred embodiment, a bar code scanner 12 is connected by a communications cable 14 that is attached to the COM port (not shown) of a general purpose computer such as a personal computer 16. The personal computer 16 includes a display monitor 13 and a keyboard 20.

It is to be understood that the bar code scanner 12 may comprise a self powered, portable unit used in conjunction with a hand held computer or microprocessor with an LCD display and a programmable memory that is preferably manufactured as a unit for use by law enforcement agencies, paramedics and other field agents in health care. The portable unit should include a small printer or be connectable to a small printer for record keeping purposes. Such devices are currently in use for inventory control and shipped package tracking and comprise a type of hardware advantageous for implementing the described system for field use.

The personal computer 16 is programmed by an application software program 15 compatible with the internal operating system of the computer that is installed from a remote source by a telecommunications link or preferably by an application software program 15 carried on a memory medium, such as the floppy disk 17. The floppy disk 17 is inserted into the disk drive slot 19 of the personal computer 16 to load the application software program 15 into the personal computer 16.

The user begins operation of the bar code identification of drugs system 10, by manipulating the mouse 18 or typing the appropriate command on the keyboard 20. This operation is represented by an item step designated by the numeral 50 on the schematic diagram shown in FIG. 3. Once activated, the computer software program 15 of the bar code identification of drugs system 10 performs hardware and software initializations necessary to activate the bar code scanner 12. In this initialization step, the computer software program 15 also prepares the bar code scanner 12 to send symbol data through the communications cable 14 after the user issues a read command from the bar code scanner 12, as indicated by the item step 52 in FIG. 3.

Before the user begins to issue read commands from the bar code scanner 12, the computer software program 15 may query the user for patient information through the video display screen 24. The user then inputs patient information data through use of the mouse 18 or the keyboard 20, as indicated in item step 54 in FIG. 3. The patient information can be used to retrieve information from a database located on the computer 16 or located on a remote computer network. Additionally, the patient information could be added to databases located on the computer 16 or located on a remote computer network, as schematically indicated by item step 56 in FIG. 3.

In the preferred embodiment, the computer software program 15 retrieves and displays graphical images 27 corresponding to the graphical images appearing in "Pictorial Guidance/Reminder System for Medication", U.S. Pat. No. 5,031,937 corresponding to the patient identified from the input patient information.

Figure 2:
FIG. 2 is a front perspective view of a tablet that has been marked with a bar code symbol capable of identification through use of the bar code identification of drugs system.
Figure 3A:
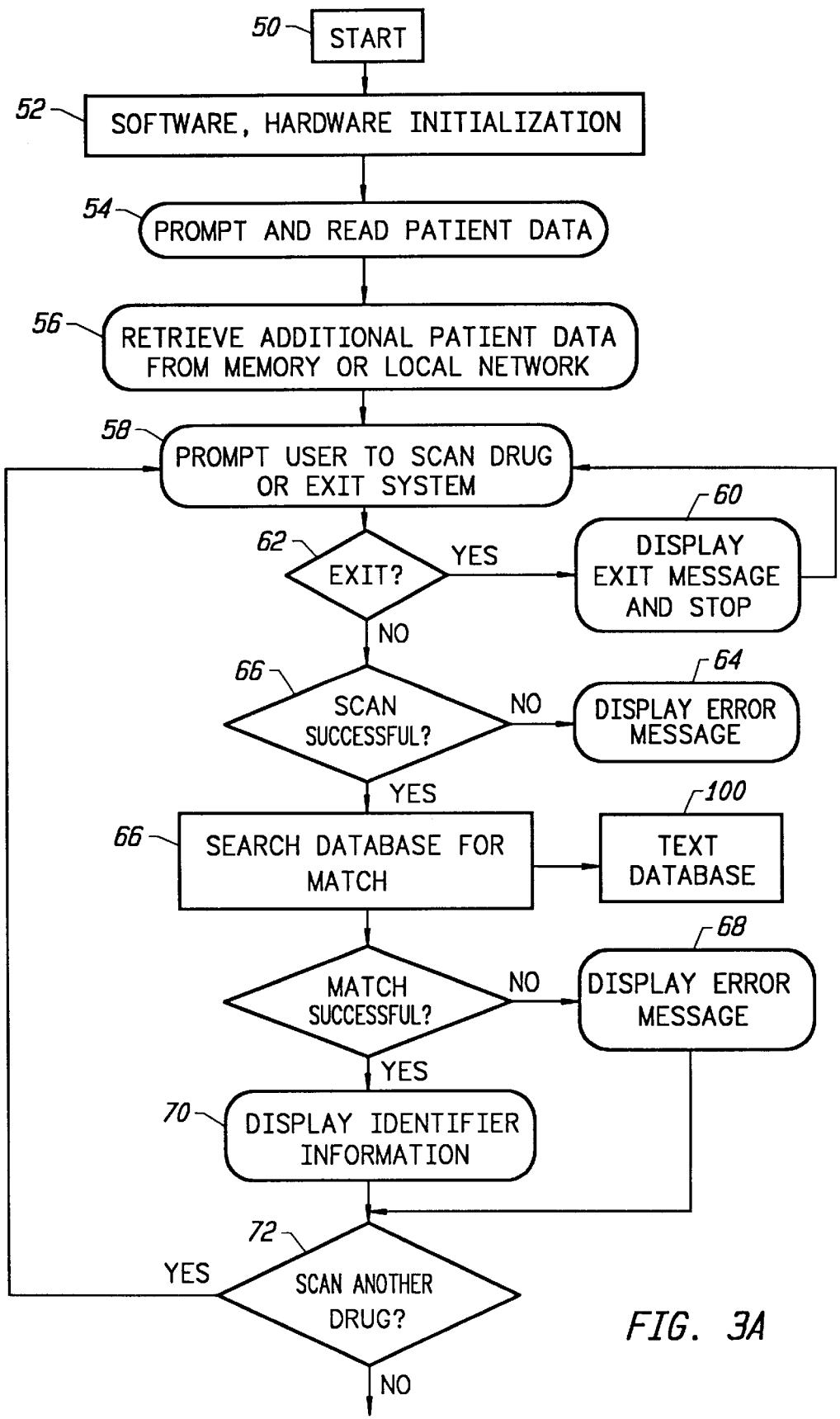
FIG. 3 is a schematic diagram of a flowchart illustrating the software logic performing the drug identification and database manipulations.
Figure 3B:
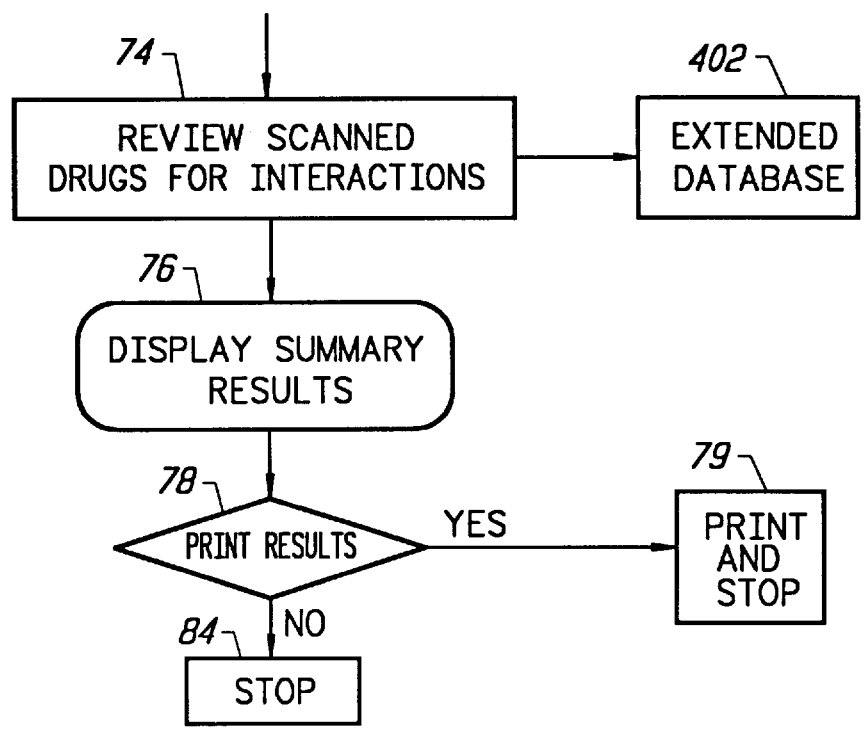

Once all necessary input patient information is complete, the video display screen 24 indicates that the user may begin to issue read commands from the bar code scanner 12, as indicated in item step 58 in FIG. 3. The user then points the face 26 of the bar code scanner 12 at the bar code symbol 42 marked on the outer surface of an exemplar medication item 40, as shown in FIG. 2. Alternatively, to stop the procedure the user issues an exit system command from the mouse 18 or keyboard 20, as indicated in item step 58 in FIG. 3.

The location of the face 26 of the bar code scanner 12 relative to the medication item 40 necessary to achieve an optimal scan will vary due to the physical specification of the bar code scanner 12, the choice of bar code symbology, and the physical dimensions of the medication 40.

Once the user has positioned the face 26 of the bar code scanner 12 relative to the medication item 40, the user issues a read command typically by pressing a trigger button 28 on the bar code scanner 12. The bar code scanner 12 analyzes the bar code symbol 42 and sends data corresponding to the bar code symbol 42 through the communications cable 14.

If the user issues an exit system command, the computer software program 15, displays an appropriate exit message and stops operation, as indicated in item step 60 in FIG. 3.

Once the user attempts a scan operation using the bar code scanner 12, the computer software program 15 first analyzes the data received from the bar code scanner 12 to check that the scan operation did not yield an error corresponding to events such as the mispositioning of the bar code scanner 12 relative to the medication item 40, as indicated in item step 60 in FIG. 3. If a scan error is detected, the computer software program 15 displays an error message and graphics on the video display screen 24 of the monitor 13 to direct the user to attempt another scan, as indicated in item step 64 in FIG. 3.

If no scan error is detected, the computer software program 15 searches through a drug identification database 100 carried within the software program 15 that typically contains a list of matching medication numeric drug identifiers and an ASCII character string that contains the name of the medication plus additional ASCII character strings and graphical images, as indicated in item step 66 in FIG. 3.

For example, a record from the drug identification database 100 might appear as:

667, 50 mg, Zoloft (sertraline HCl), Pfizer, Roerig Division meaning that the computer software program 15 would interpret a bar code symbol 42 that was decoded into the medication identifier integer value 667 as 50 milligrams of the medication "Zoloft".

The result of the database search will indicate whether a successful match was found. If the match was unsuccessful, an error message is shown on the display screen 24, as indicated in item step 68 in FIG. 3. If the match is successful, information corresponding to the medication item 40 is shown on the display screen 24, as indicated in item step 70 in FIG. 3. The display screen 24 then prompts the user to scan another medication or to create an informational summary report 71 on the display screen 24, as indicated in item step 72 in FIG. 3.

Once the user requests an information report 71, the computer software program 15 first performs a comparison of the set of medications scanned with reference to an extended database 102 containing known harmful medication side effects and interactions, as indicated in item step 74 in FIG. 3. The information report 71 includes information regarding possible harmful medication interactions, is then shown as a report on the display screen 24, as indicated in item step 76 in FIG. 3. The computer software program 15 then displays a request for the user to indicate if a printed record is requested at the step 78. If yes, then a printed record is generated at item step 79 by a printer 80 in communication with the computer 16 by a communication link, here a cable 82.

As noted, the system may be used with a portable unit that because of memory limitations only identifies the drug using the text database 100 and does not include the extended database 102 that contains data related to specific patients, to graphical images or to adverse side effects and harmful interactions. Once the report is printed, the computer software program 15 then stops. If after the inquiry at step 84 no report is requested, then the software program stops at step 84 after display of the report at item step 76.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A computerized drug identification system for the identification of medication items in pill, capsule, tablet, and caplet form, comprising:

a plurality of medication items, each medication item having an outer surface marked with a machine scannable bar code symbol identifying the medication item;

scanner means for electronically scanning the bar code symbol and decoding the bar code symbol into binary data;

a general purpose computer having a random access memory and a database of medication identifier codes;

means for transmitting the binary data from the scanner means to the random access memory of the computer;

means for processing the binary data in the random access memory of the computer and comparing the processed binary data to the database of medication identifier codes to match the processed binary data with a medication identifier code; and means for display of the medication identification data associated with the matched medication identifier code.

2. The computerized drug identification system of claim 1 wherein the system contains means for computer input of patient identifier information.

3. The computerized drug identification system of claim 2 wherein the database of medication identifier codes contains patient identifier information supplied by the user.

4. The computerized drug identification system of claim 1 wherein the system displays a pictorial graphic of the medication item.

5. The computerized drug identification system of claim 4 wherein the system contains a database of harmful medication interaction identifiers, wherein the system displays an information report indicating the set of scanned medication items that includes a combination appearing in the database of harmful medication interaction identifiers.

* * * * *